(12) United States Patent
Sanders

(10) Patent No.: US 7,684,861 B2
(45) Date of Patent: Mar. 23, 2010

(54) IMPLANTABLE CARDIAC MONITOR UPGRADEABLE TO PACEMAKER OR CARDIAC RESYNCHRONIZATION DEVICE

(75) Inventor: Richard S. Sanders, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 930 days.

(21) Appl. No.: 10/712,776

(22) Filed: Nov. 13, 2003

(65) Prior Publication Data

US 2005/0107839 A1 May 19, 2005

(51) Int. Cl.
A61N 1/36 (2006.01)
(52) U.S. Cl. ............................................. 607/9; 607/30
(58) Field of Classification Search .................... 607/4, 607/5, 14, 30, 32, 123, 9, 27, 28
See application file for complete search history.

(56) References Cited

U.S. PATENT DOCUMENTS

| | | | |
|---|---|---|---|
| 4,585,004 A | | 4/1986 | Brownlee |
| 4,662,382 A | * | 5/1987 | Sluetz et al. ................ 607/126 |
| 4,686,988 A | * | 8/1987 | Sholder ........................ 607/28 |
| 5,024,221 A | * | 6/1991 | Morgan ........................ 607/10 |
| 5,113,869 A | | 5/1992 | Nappholz et al. |
| 5,265,602 A | | 11/1993 | Anderson et al. |
| 5,324,310 A | | 6/1994 | Greeninger et al. |
| 5,331,966 A | | 7/1994 | Bennett et al. |
| 5,360,437 A | | 11/1994 | Thompson |
| 5,439,481 A | * | 8/1995 | Adams ........................... 607/5 |
| 5,456,692 A | | 10/1995 | Smith, Jr. et al. |
| 5,687,737 A | * | 11/1997 | Branham et al. ............ 600/523 |
| 5,725,559 A | | 3/1998 | Alt et al. |
| 5,843,138 A | | 12/1998 | Evers et al. |
| 5,935,081 A | | 8/1999 | Kadhiresan |

(Continued)

FOREIGN PATENT DOCUMENTS

EP 0308536 A1 3/1989

(Continued)

OTHER PUBLICATIONS

"New Diagnostic Tool—Reveal Insertable Loop Recorder", http://www.medtronic.com/reveal/new.html (Archived Sep. 19, 2000),3 Pages.

(Continued)

Primary Examiner—George R Evanisko
Assistant Examiner—Michael Kahelin
(74) Attorney, Agent, or Firm—Schwegman, Lundberg & Woessner, P.A.

(57) ABSTRACT

An implantable cardiac monitor upgradeable to an implantable pacemaker or an implantable cardiac resynchronization device allows the use of a single implantable medical device for monitoring cardiac conditions and later, if needed, for cardiac pacing. The implantable medical device includes a circuit that can be configured, by programming through an external programmer, to either the implantable cardiac monitor or the implantable pacemaker. The implantable medical device is first configured to and used as the implantable cardiac monitor for acquisition of physiological data indicative of a need for a pacing therapy. If the pacing therapy is to follow, the implantable medical device is reconfigured from the implantable cardiac monitor to the implantable pacemaker, thus eliminating the need of using two implantable medical devices.

20 Claims, 7 Drawing Sheets

U.S. PATENT DOCUMENTS

| | | | |
|---|---|---|---|
| 6,073,049 A | 6/2000 | Alt et al. | |
| 6,088,618 A | 7/2000 | Kerver | |
| 6,157,859 A | 12/2000 | Alt | |
| 6,201,993 B1 * | 3/2001 | Kruse et al. | 607/30 |
| 6,405,083 B1 | 6/2002 | Rockwell et al. | |
| 6,477,417 B1 * | 11/2002 | Levine | 607/9 |
| 6,480,733 B1 | 11/2002 | Turcott | |
| 6,505,067 B1 | 1/2003 | Lee et al. | |
| 6,589,187 B1 * | 7/2003 | Dirnberger et al. | 600/508 |
| 6,636,963 B1 * | 10/2003 | Stein et al. | 713/1 |
| 6,658,283 B1 | 12/2003 | Bornzin et al. | |
| 6,889,079 B2 * | 5/2005 | Bocek et al. | 607/9 |
| 6,925,326 B1 * | 8/2005 | Levine et al. | 600/510 |
| 6,954,671 B1 * | 10/2005 | Hoijer et al. | 607/9 |
| 2002/0058906 A1 * | 5/2002 | Lebel et al. | 604/65 |
| 2002/0072778 A1 | 6/2002 | Guck et al. | |
| 2003/0083586 A1 | 5/2003 | Ferek-Petric | |
| 2004/0230229 A1 * | 11/2004 | Lovett et al. | 607/4 |
| 2005/0197674 A1 | 9/2005 | McCabe et al. | |

FOREIGN PATENT DOCUMENTS

| | | |
|---|---|---|
| EP | 744190 | 11/1996 |
| EP | 0784996 A1 | 7/1997 |
| WO | WO-9401173 A1 | 1/1994 |
| WO | WO-2005089643 A1 | 9/2005 |

OTHER PUBLICATIONS

Hughes, Howard C., et al., "The Effects of Electrode Position on the Detection of the Transvenous Cardiac Electrogram", *PACE*, vol. 3, (Nov.-Dec. 1980), 651-655.

Leitch, James, et al., "Feasibility of an implantable arrhythmia monitor", *PACE*, vol. 15, No. 12, (Dec. 1992), 2232-5.

Mazur, Alexander, "Functional similarity between electrograms recorded from an implantable cardioverter defibrillator emulator and the surface electrocardiogram", *PACE*, vol. 24, (Jan. 2001), 34-40.

Theres, Heinz, et al., "Electrogram signals recorded from acute and chronic pacemaker implantation sites in pacemaker patie", *PACE*, vol. 21, Part 1, (Jan. 1998), 11-17.

Zhang, Yi, "Rejection of Noises Caused by Postural Changes During Acute Myocardial Infarction Detection", U.S. Appl. No. 11/275,800, Date mailed Jan. 30, 2006, 60 pages.

"U.S. Appl. No. 10/795,126, Non final office action mailed Jan. 25, 2007", 17 pgs.

"U.S. Appl. No. 10/795,126, Notice of allowance mailed Jul. 9, 2007", 10 pgs.

"U.S. Appl. No. 10/795,126, Response filed Apr. 25, 2007 to Non final office action mailed Jan. 25, 2007", 11 pgs.

* cited by examiner

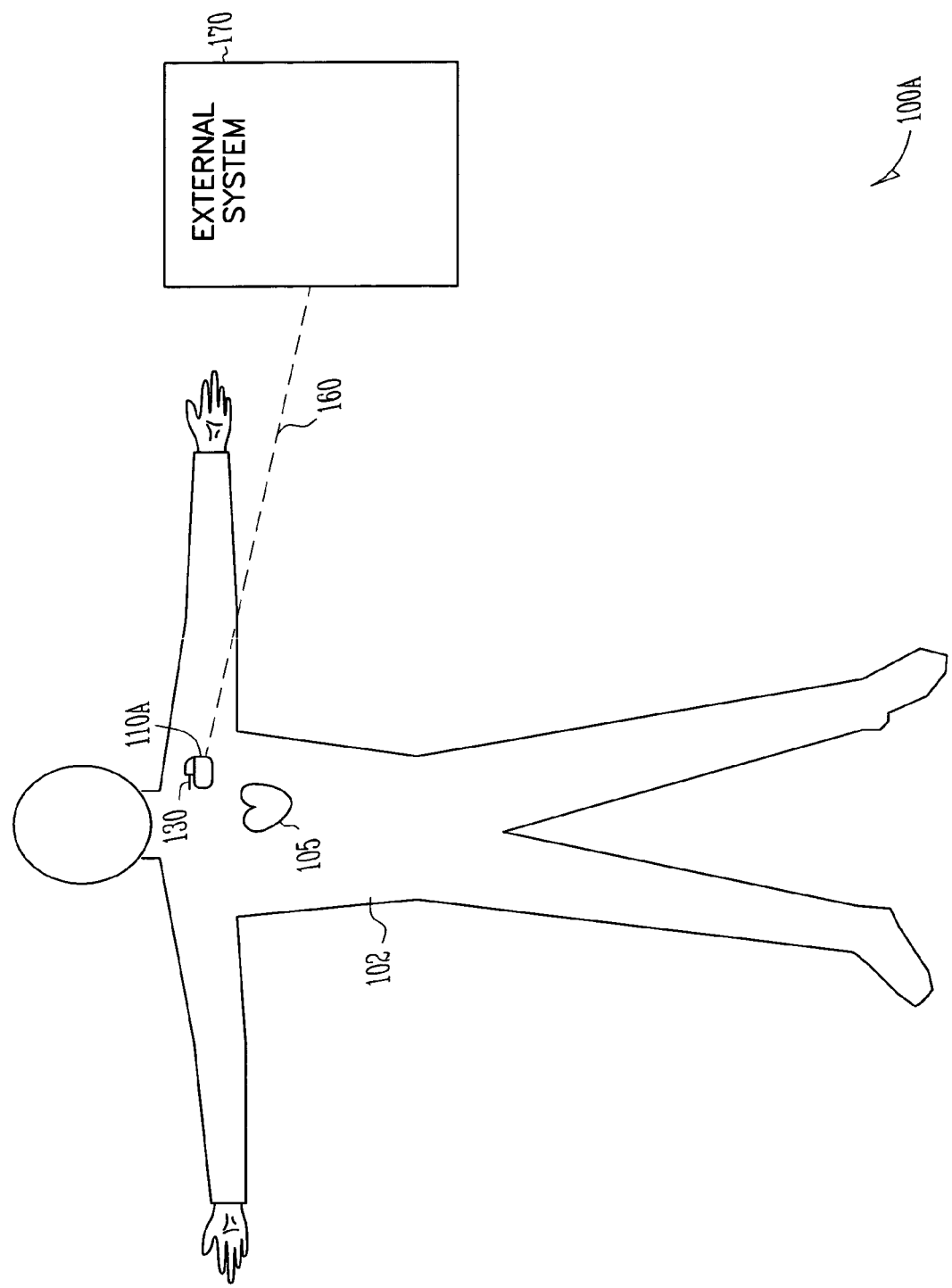

IMPLANTABLE CARDIAC MONITOR UPGRADEABLE TO PACEMAKER OR CARDIAC RESYNCHRONIZATION DEVICE

TECHNICAL FIELD

This document generally relates to cardiac rhythm management systems and particularly, but not by way of limitation, to such systems including an implantable cardiac monitor that is upgradeable to an implantable pacemaker or an implantable cardiac resynchronization device.

BACKGROUND

A heart is the center of a person's circulatory system. It includes a complex electromechanical system performing two major pumping functions. The left portions of the heart, including the left atrium and the left ventricle, draw oxygenated blood from the lungs and pump it to the organs of the body to provide the organs with their metabolic needs for oxygen. The right portions of the heart, including the right atrium and the right ventricle, draw deoxygenated blood from the body organs and pump it to the lungs where the blood gets oxygenated. These pumping functions are accomplished by contractions of the myocardium, i.e., heart muscles. In a normal heart, the sinoatrial (SA) node, the heart's natural pacemaker, generates electrical impulses, called action potentials, that propagate through an electrical conduction system to various regions of the heart to excite the muscular tissue of these regions. Coordinated delays in the propagations of the action potentials in a normal electrical conduction system cause the various portions of the heart to contract in synchrony to result in efficient pumping functions. A blocked or otherwise abnormal electrical conduction and/or a deteriorated myocardium cause asynchronous contraction of the heart, and result in poor hemodynamic performance including diminished blood supply to the body.

Implantable pacemakers have been used to treat patients suffering from, for example, an abnormal SA node, a dysfunctional electrical conduction system, and/or a deteriorated myocardium. A pacemaker generates electrical pulses that substitute for the action potentials to excite the myocardium. The electrical pulses are delivered to one or more sites in or about the heart through one or more pacing leads with electrodes, bypassing at least a portion of the natural electrical conduction system. The effectiveness of a pacing therapy using an implantable pacemaker in improving a patient's hemodynamic performance depends on the patient's particular cardiac and other physical conditions.

To predict whether a patient will benefit from a pacing therapy delivered by an implantable pacemaker, the patient's physiological and/or pathological conditions are evaluated. The evaluation becomes difficult when the patient's abnormal conditions, or symptoms, occur occasionally or intermittently. For example, for a patient suffering from recurrent fainting, it often occurs that when the patient sees a physician, the symptoms are not present, and the physician is unable to determine what caused the fainting. A solution is to use an implantable cardiac monitor that records the patient's electrocardiogram during detected episodes of abnormal conditions. The recorded electrocardiogram provides the physician with information needed to determine the cause of the symptoms and to predict whether the patient will likely benefit from the pacing therapy.

One problem is, however, that if the patient is indicated for cardiac pacing therapy, the implantable cardiac monitor needs to be explanted, and an implantable pacemaker needs to be implanted. That is, two separate implantable medical devices are needed, imposing a high cost upon the patient or another responsible party, such as an insurer or a hospital.

SUMMARY

An implantable cardiac monitor upgradeable to an implantable pacemaker (including an implantable cardiac resynchronization device) allows the use of a single implantable medical device for monitoring cardiac conditions and later, if needed, for cardiac pacing. The implantable medical device includes a circuit that can be configured, by programming through an external programmer, to either the implantable cardiac monitor or the implantable pacemaker. The implantable medical device is first configured to and used as the implantable cardiac monitor for acquisition of physiological data indicative of a need for a pacing therapy. If the pacing therapy is to be delivered, the implantable medical device is reconfigured from the implantable cardiac monitor to the implantable pacemaker, thus eliminating the need for two implantable medical devices.

In one embodiment, an implantable medical device includes a sensing circuit, a pacing circuit, and a processor. The sensing circuit senses at least one electrogram. The pacing circuit delivers pacing pulses to a heart when being programmed for pacing. The processor includes a cardiac monitor controller that is upgradeable to a pacemaker controller by programming the implantable medical device. The sensing circuit is programmable from a circuit suitable for far-field electrogram sensing to a circuit suitable for intracardiac electrogram sensing when the cardiac monitor controller is upgraded to the pacemaker controller.

In one embodiment, an implantable adaptor includes an implantable electrode, an implantable connector, and an adaptor body. The implantable electrode is suitable for far-field electrogram sensing. The implantable connector provides a detachable connection between the implantable electrode and an implantable cardiac rhythm management (CRM) device. The adaptor body connects the implantable electrode and the implantable connector.

In one embodiment, an implantable medical device programmer includes a device configuration module and a telemetry module. The device configuration module generates instructions for configuring an implantable medical device into an implantable cardiac monitor or an implantable pacemaker. The telemetry module transmits the instructions to the implantable medical device.

In one embodiment, a system includes an implantable CRM device and an implantable adaptor. The CRM device includes a device body and a header. The device body encapsulates a CRM circuit upgradeable from a monitoring circuit to a pacing circuit after the implantation of the implantable CRM device. The header is attached to the device body and includes at least one connector providing for electrical connection to the CRM circuit. The implantable adaptor is to be connected to the header and includes an electrode suitable for sensing a far-field electrogram.

In one embodiment, a method includes generating instructions for upgrading an implantable cardiac monitor to an implantable pacemaker and transmitting the instructions to the implantable cardiac monitor via telemetry. In one embodiment, the instructions include computer-executable instructions, stored in a computer-readable medium, to cause a computer or computer-based system to perform the method.

In one embodiment, a method includes generating instructions for converting an implantable pacemaker to an implantable cardiac monitor and transmitting the instructions to the implantable pacemaker. In one embodiment, the instructions include computer-executable instructions, stored in a computer-readable medium, to cause a computer or computer-based system to perform the method.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in the present document.

FIG. 1A is an illustration of an embodiment of a cardiac monitoring system, including an implantable cardiac monitor, and portions of an environment in which the system is used.

DETAILED DESCRIPTION

Figure 1B:
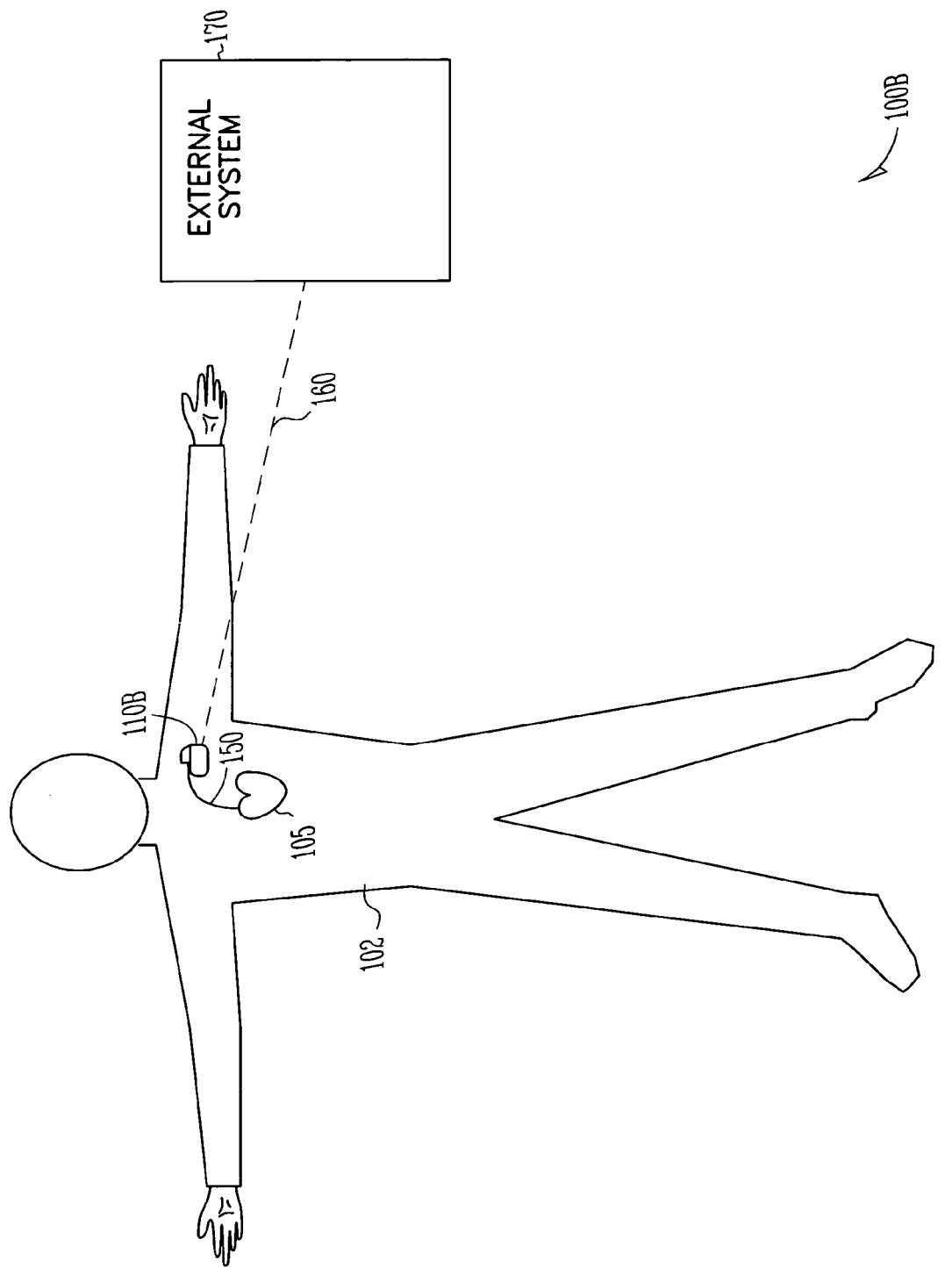
FIG. 1B is an illustration of an embodiment of a cardiac pacing system, including an implantable pacemaker, and portions of an environment in which the system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

This document discusses, among other things, a cardiac rhythm management system including an implantable medical device that is configurable to either an implantable cardiac monitor or an implantable pacemaker. The implantable pacemaker includes an implantable cardiac resynchronization device. The configuration is performed by programming the implantable medical device using an external programmer wirelessly communicating with the implantable medical device via telemetry. In one embodiment, the implantable medical device is initially implanted in a patient as the implantable cardiac monitor. Later, when the patient needs a pacing therapy, the implantable cardiac monitor is upgraded to the implantable pacemaker by re-configuration using the external programmer. The implantable cardiac monitor monitors physiological signals of a patient possibly suffering an abnormal cardiac condition treatable by cardiac pacing, and stores at least the physiological signals recorded when the abnormal cardiac condition is detected. In one example, the patient suffers brief periods of syncope, during which the patient faints. The implantable cardiac monitor records electrocardiogram indicative of the underlying pathological conditions such as cardiac arrhythmia. The recorded physiological signals, such as an electrocardiogram and a physical activity level, are later analyzed by an external system and/or a physician. If the recorded physiological signals indicate an underlying pathological condition treatable by a pacing therapy, the implantable cardiac monitor can be upgraded to the implantable pacemaker or an implantable cardiac resynchronization device. In another example, the implantable cardiac monitor is used to track a progression of heart failure. If and when the degree of the heart failure develops to a certain level where the patient can benefit from a pacing therapy, the implantable cardiac monitor can be upgraded to an implantable pacemaker or an implantable cardiac resynchronization device. Using such an re-configurable/upgradeable device eliminates the need for two separate implantable devices, thus reducing the overall cost. Implantation of intracardiac pacing leads is required only after the determination that the patient will receive the pacing therapy.

In this document, a "user" includes a physician or other caregiver treating a patient by using the implantable medical device that is upgradeable from the implantable cardiac monitor to the implantable pacemaker. An "intracardiac electrogram" includes an electrocardiogram recorded using electrodes disposed in and/or on the heart. A "far-field electrogram" includes an electrocardiogram recorded using electrodes implanted within the body of a patient but away from the heart. An "implantable pacemaker" includes an implantable cardiac resynchronization device or any other implantable medical device capable of delivering at least one cardiac pacing therapy.

FIG. 1A is an illustration of an embodiment of a cardiac monitoring system 100A and portions of an environment in which the system is used. Cardiac monitoring system 100A includes an implantable cardiac monitor 110A, an adaptor 130, an external system 170, and a wireless telemetry link 160.

Implantable cardiac monitor 110A is an implantable medical device configured to an implantable cardiac monitor for recording physiological signals. The physiological signals include one or more far-field electrograms. In one embodiment, the physiological signals also include a signal indicative of a patient's physical activity level or metabolic level, such as an acceleration signal. In one embodiment, the implantable medical device is capable of being configured to implantable cardiac monitor 110A, and later reconfigured by a software upgrade to an implantable pacemaker. In another embodiment, the implantable medical device is initially configured as the implantable pacemaker during the manufacturing process. It is then configured to implantable cardiac monitor 110A by a user before implantation in a patient, and later converted back to the implantable pacemaker by the user when the patient's need for a pacing therapy is indicated after the implantation.

Adaptor 130 includes one or more far-field electrogram sensing electrodes and provides an electrical and mechanical interface between implantable cardiac monitor 110A and the sensing electrodes. In one embodiment, one or more far-field electrograms are sensed through electrodes incorporated into adaptor 130. In another embodiment, the far-field electrograms are sensed through one or more electrodes incorporated into adaptor 130 and one or more electrodes incorporated into implantable cardiac monitor 110A. As shown in FIG. 1A, implantable cardiac monitor 110A is implanted in a body 102, in a location near a heart 105, to allow proper far-field electrogram sensing, and possibly at a later time, delivering of pacing pulses heart 105 through pacing leads. In one embodiment, the location and orientation of implantable cardiac monitor 110A in body 102 depend on needs for proper sensing of the physiological signals such as the far-field electrograms and the acceleration signal.

External system 170 communicates with implantable cardiac monitor 110A. It allows a user and/or a patient to control the operation of implantable cardiac monitor 110A, including its upgrade into the implantable pacemaker. In one embodiment, external system 170 includes a programmer. In another embodiment, external system 170 includes an advanced patient management system, such as discussed in U.S. patent application Ser. No. 10/323,604, "ADVANCED PATIENT MANAGEMENT FOR DEFINING, IDENTIFYING AND USING PREDETERMINED HEALTH-RELATED EVENTS," filed on Dec. 18, 2002, assigned to Cardiac Pacemakers, Inc., the specification of which is incorporated herein by reference in its entirety. The advanced patient management system allows the user to access to implantable cardiac monitor 110A, or to communicate with the patient, from a remote location.

Telemetry link 160 is a wireless communication link connecting implantable cardiac monitor 110A and external system 170. In one embodiment, telemetry link 160 is an inductive telemetry link. In an alternative embodiment, telemetry link 160 is a far-field radio-frequency telemetry link. In one embodiment, telemetry link 160 provides for data transmission from implantable cardiac monitor 110A to external system 170. This may include, for example, transmitting real-time physiological data acquired by implantable cardiac monitor 110A, extracting physiological data acquired by and stored in implantable cardiac monitor 110A, and extracting data indicating an operational status of implantable cardiac monitor 110A (e.g., battery status and electrode impedance). In a further embodiment, telemetry link 160 provides for data transmission from external system 170 to implantable cardiac monitor 110A. This may include, for example, programming implantable cardiac monitor 110A to acquire physiological data, programming implantable cardiac monitor 110A to perform at least one self-diagnostic test (such as for a device operational status), and configuring implantable cardiac monitor 110A to the implantable pacemaker by programming it.

FIG. 1B is an illustration of an embodiment of a cardiac pacing system 100B and portions of an environment in which the system is used. Cardiac monitoring system 100B includes an implantable pacemaker 110B, a lead system 150, external system 170, and wireless telemetry link 160.

Implantable pacemaker 110B is an implantable medical device configured to an implantable pacemaker for delivering one or more pacing therapies. In one embodiment, implantable pacemaker 110B is configured based on the same implantable medical device configured to implantable cardiac monitor 110A. In one specific embodiment, the implantable medical device is upgraded, after implantation, from implantable cardiac monitor 110A to implantable pacemaker 110B. Examples of pacing therapies provided by implantable pacemaker 110B include, but are not limited to, anti-bradycardia pacing, anti-tachycardia pacing, and cardiac resynchronization therapy.

Lead system 150 provides electrical connections between implantable pacemaker 110B and heart 105. It includes one or more pacing leads each having one or more electrodes for sensing intracardiac electrogram and delivering pacing pulses. In one embodiment, after being upgraded from implantable cardiac monitor 110A, implantable pacemaker 110B remains in about the same location in body 102, and adopter 130 is replaced with lead system 150.

The implantable medical device includes a telemetry module supporting telemetry link 160. This telemetry module remains substantially the same after the implantable medical device is upgraded from implantable cardiac monitor 110A to implantable pacemaker 110B. Thus, the same external system 170 communicates with implantable pacemaker 110B via telemetry link 160. In one embodiment, telemetry link 160 provides for data transmission from implantable pacemaker 110B to external system 170. This may include, for example, transmitting real-time physiological data acquired by implantable pacemaker 110B, extracting physiological data acquired by and stored in implantable pacemaker 110B, extracting therapy history data stored in implantable pacemaker 110B, and extracting data indicating an operational status of implantable pacemaker 110B (e.g., battery status and lead impedance). In a further embodiment, telemetry link 160 provides for data transmission from external system 170 to implantable pacemaker 110B. This may include, for example, programming implantable pacemaker 110B to acquire physiological data, programming implantable pacemaker 110B to perform at least one self-diagnostic test (such as for a device operational status), programming implantable pacemaker 110B to deliver at least one therapy, and converting implantable pacemaker 110B back to implantable cardiac monitor 110A by programming.

Figure 2:
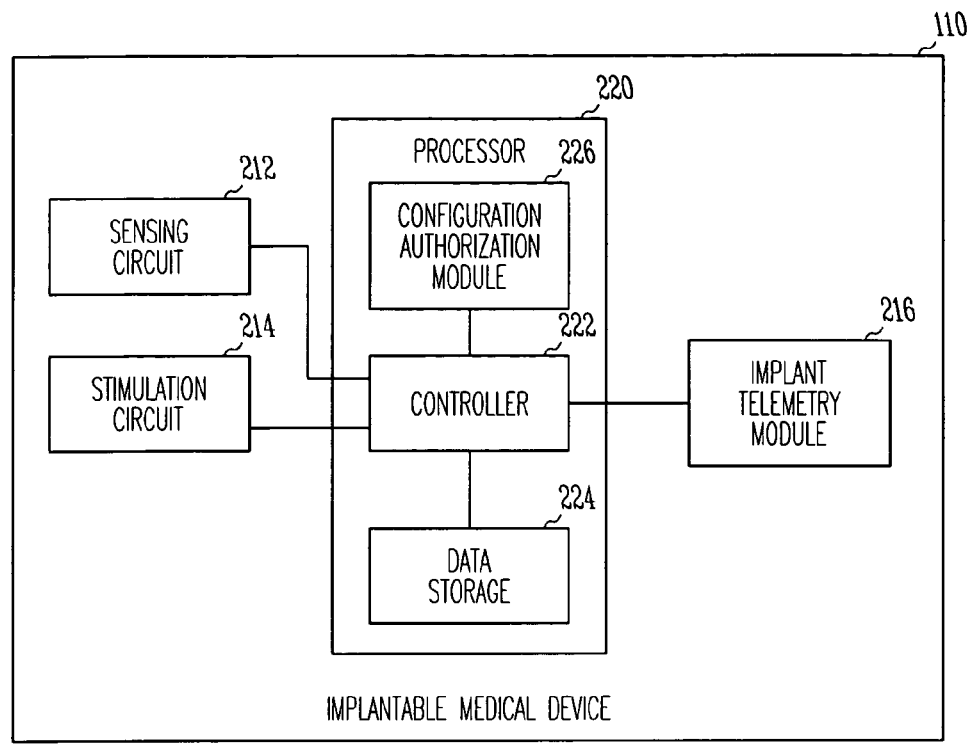
FIG. 2 is a block diagram illustrating one embodiment of a circuit of an implantable medical device that is configurable to either the implantable cardiac monitor or the implantable pacemaker.

FIG. 2 is a block diagram illustrating one embodiment of a circuit of an implantable medical device 110 that is configurable to implantable cardiac monitor 110A or implantable pacemaker 10B. Implantable medical device 110 includes a sensing circuit 212, a stimulation circuit 214, an implant telemetry module 216, and a processor 220.

Sensing circuit 212 allows for sensing of the physiological signals such as the electrogram and the physical activity level. Sensing circuit 212 includes an electrogram sensing circuit that allows for far-field electrogram sensing when implantable medical device 110 is configured to and used as implantable cardiac monitor 110A and intracardiac electrogram sensing when implantable medical device 110 is configured to and used as implantable pacemaker 110B. Sensing circuit 212 includes an amplifier and a band-pass filter. In one embodiment, the cutoff frequencies of the band-pass filter is programmable. In one specific embodiment, the band-pass filter includes two band-pass filters, one having cutoff frequencies suitable for far-field electrogram sensing and the other having cutoff frequencies suitable for intracardiac electrogram sensing. In another embodiment, the band-pass filter includes a digital filter having filter coefficients programmable for either cutoff frequencies suitable for far-field electrogram sensing or cutoff frequencies suitable for intracardiac electrogram sensing. In one embodiment, the band-pass filter suitable for far-field electrogram sensing has a low cutoff frequency in a range of 0.5 Hz to 10 Hz and a high cutoff frequency in a range of 30 Hz to 100 Hz; and the band-pass filter suitable for intracardiac electrogram sensing has a low cutoff frequency in a range of 10 Hz to 30 Hz and a high cutoff frequency in a range of 60 Hz to 150 Hz. In one embodiment, sensing circuit 212 also includes an activity sensor circuit that allows for sensing of one or more signals indicative of a physical activity level and or a metabolic level of the patient. In one specific embodiment, sensing circuit 212 includes at least one accelerometer and a circuit conditioning the acceleration signal.

Stimulation circuit 214 produces and delivers electrical stimulation pulses, such as constant voltage or constant current pulses with programmable amplitude and pulse width. In one embodiment, stimulation circuit 214 includes a pacing output circuit. When implantable medical device 110 is configured to implantable cardiac monitor 110A, stimulation circuit 214 is inactive. When implantable medical device 110 is configured to implantable pacemaker 110B, stimulation circuit 214 is capable of producing pacing pulses as controlled by processor 220.

Implant telemetry module 216 includes an antenna and a transceiver to support two-way communications via telemetry link 160. This portion of implantable medical device 110 remains substantially the same when implantable medical device 110 is configured from implantable cardiac monitor 110A to implantable pacemaker 110B, or vice versa. In one embodiment, the speed for transmitting the acquired physiological signal via telemetry link 160, in terms of the ratio of transmission time to recording time, depends on the bandwidth of the acquired physiological signal.

Processor 220 includes a controller 222, a data storage 224, and a configuration authorization module 226. Controller 222 controls the operation of sensing circuit 212, stimulation circuit 214, and implant telemetry module 216. Controller 222 can be configured by programming to control cardiac monitoring and/or stimulation functions. To configure implantable medical device 110 from implantable cardiac monitor 110A to implantable pacemaker 110B, or vice versa, device configuration instructions sent from external system 170 are received through implant telemetry module 216, causing controller 222 to convert from a cardiac monitor controller to a pacemaker controller, or vice versa. In one embodiment, the configuration is achieved by letting a new code overwrite at least portions of an existing code. In another embodiment, controller 222 contains both a cardiac monitor control code and a pacemaker control code, and a command from external system 170 activates one of the codes. Data storage 224 stores the physiological signals acquired by implantable medical device 110 (either as implantable cardiac monitor 110A or implantable pacemaker 110B). In one embodiment, controller 222 includes an activity detector to detect predetermined types of activities from the acquired physiological signals, and data storage 224 stores an activity log tracking occurrences of the detected activities. In one embodiment, the acquired physiological signals are stored in data storage 224 only when the activity detector detects activities of a predetermined type. In one specific example, controller 222 includes an arrhythmia detector to detect predetermined types of arrhythmia from a recorded electrogram, and data storage 224 stores segments of the electrogram being the detected arrhythmic episodes and an activity log reporting type and time of each detected arrhythmic episode. In another embodiment, the acquired physiological signals are also stored in data storage 224 according to a command sent from external system 170. Configuration authorization module 226 protects implantable medical device 110 from being configured by accident or mistake, such as by noise, interference, or instructions for configuration intended for a different implantable medical device. In one embodiment, the device configuration instructions sent from external system 170 include authorization information such as a password or a device identification code uniquely identifying the device intended to be configured. Configuration authorization module 226 permits controller 222 to be configured upon verifying the authorization information. In another embodiment, implantable medical device 110 receives an authorization signal from external system 170 before an intended device configuration. The authorization signal includes the authorization information such as the password or the device identification code. External system 170 sends the device configuration instructions to implantable medical device 110 after receiving a permission signal generated by configuration authorization module 226 upon verifying the authorization information.

In one embodiment, processor 220, including controller 222 and data storage 224, is implemented with a microprocessor and a memory circuit. The memory circuit includes a read-only memory (ROM) to store firmware and a random-access memory (RAM) to store an upgradeable software and data including those representing the acquired physiological signals. The firmware includes a control code that remains unchanged after implantable medical device 110 is manufactured. At least a portion of the software is updated every time when controller 222 is converted from the cardiac monitor controller to the pacemaker controller, or vice versa. A basic or default control code, as the firmware and possibly also a portion of the software, is initially installed and always remains in implantable medical device 110. In one embodiment, the basic or default control code provides for a safety operation mode when implantable medical device 110 is being upgraded from implantable cardiac monitor 110A to implantable pacemaker 110B or being converted from implantable pacemaker 110B to implantable cardiac monitor 110A. In one embodiment, the safety operation mode includes an "idle" mode preparing implantable medical device for configuration by programming. The overall size of the RAM depends on the size of the software and the amount of the data required to store. The data storage space in the RAM may be reallocated when necessary. For example, it is possible that when implantable medical device 110 is configured from implantable cardiac monitor 110A to implantable pacemaker 110B, more RAM space for control code but less space for data is necessary.

Figure 3A:
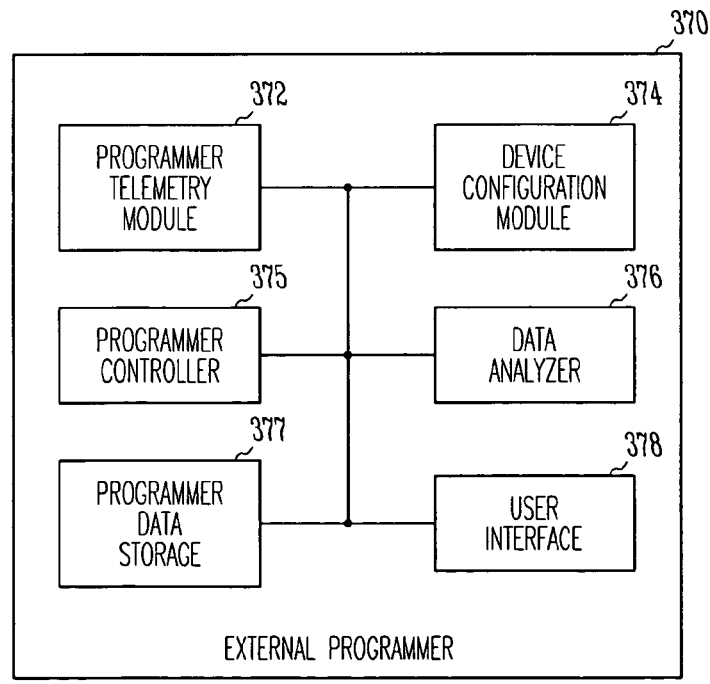
FIG. 3A is a block diagram showing one embodiment of a circuit of an external programmer communicating with the implantable medical device.

FIG. 3A is a block diagram showing one embodiment of a circuit of an external programmer 370 communicating with implantable medical device 110 via telemetry link 160. In one embodiment, programmer 370 is external system 170. In another embodiment, programmer 370 is an element of external system 170 that directly communicates with implantable medical device 110. Programmer 370 includes an programmer telemetry module 372, a device configuration module 374, a programmer controller 375, a data analyzer 376, a programmer data storage 377, and a user interface 378.

Programmer telemetry module 372 includes an antenna and a transceiver to support two-way communications via telemetry link 160. Programmer telemetry module 372 and implant telemetry module 216 form telemetry link 160.

Device configuration module 374 generates instructions for configuring implantable medical device 110 to implantable cardiac monitor 110A or implantable pacemaker 110B, including updating implantable cardiac monitor 110A to implantable pacemaker 110B, or converting implantable pacemaker 110B to implantable cardiac monitor 110A. In one embodiment, the instructions include new control code that overwrites at least portions of the control code stored in implantable medical device 110. In another embodiment, the instructions include commands for activating some portions, and deactivating some other portions, of the control code stored in implantable medical device 110. In one embodiment, the instructions include a code selecting or programming the band-pass filter of sensing circuit 212. In one embodiment, the instructions include a code allocating or reallocating RAM space for storage of the control code and data including those representing the acquired physiological signals and device status.

Programmer controller 375 controls the overall operation of programmer 370. In one embodiment, programmer 370 is a computer-based device. Programmer controller 375 includes at least portions of the computer's central processing unit and coordinates the activities of all the elements of programmer 370.

Data analyzer 376 processes data stored in programmer data storage 377, i.e., data acquired by implantable medical device 110 and transmitted to programmer 370 via telemetry link 160. The processed data are presented to the user through user interface 378. In one embodiment, data analyzer 376 further analyzes the processed data to detect certain predetermined cardiac conditions to provide the user with a basis for determining whether the patient will likely benefit from the pacing therapy. In one specific embodiment, data analyzer 376 includes one or more arrhythmia detectors to detect and/or classify predetermined types of cardiac arrhythmia.

User interface 378 includes a display screen to present data acquired by implantable medical device 110, indication of the operative status of implantable medical device 110, and operating parameters for implantable medical device 110. In one embodiment, the display screen is an interactive screen, through which the user enters a command or a parameter to control the operation of implantable medical device 110. In another embodiment, user interface 378 includes user-input devices such as a keyboard, a mouse, a track ball, and/or a touch pad to receive the command or parameter from the user. In one embodiment, user interface 378 includes a device reset key allowing the user to reset implantable medical device 110 by forcing it to run the basic or default control code, i.e., to operate in the safety operation mode. In one embodiment, user interface 378 includes an device authorization input to accept the authorization information, such as the password or the device identification code, required before implantable medical device 110 is allowed to be configured or reconfigured by programming. In one embodiment, device configuration module 374 is activated only upon receipt of the authorization information.

Figure 3B:
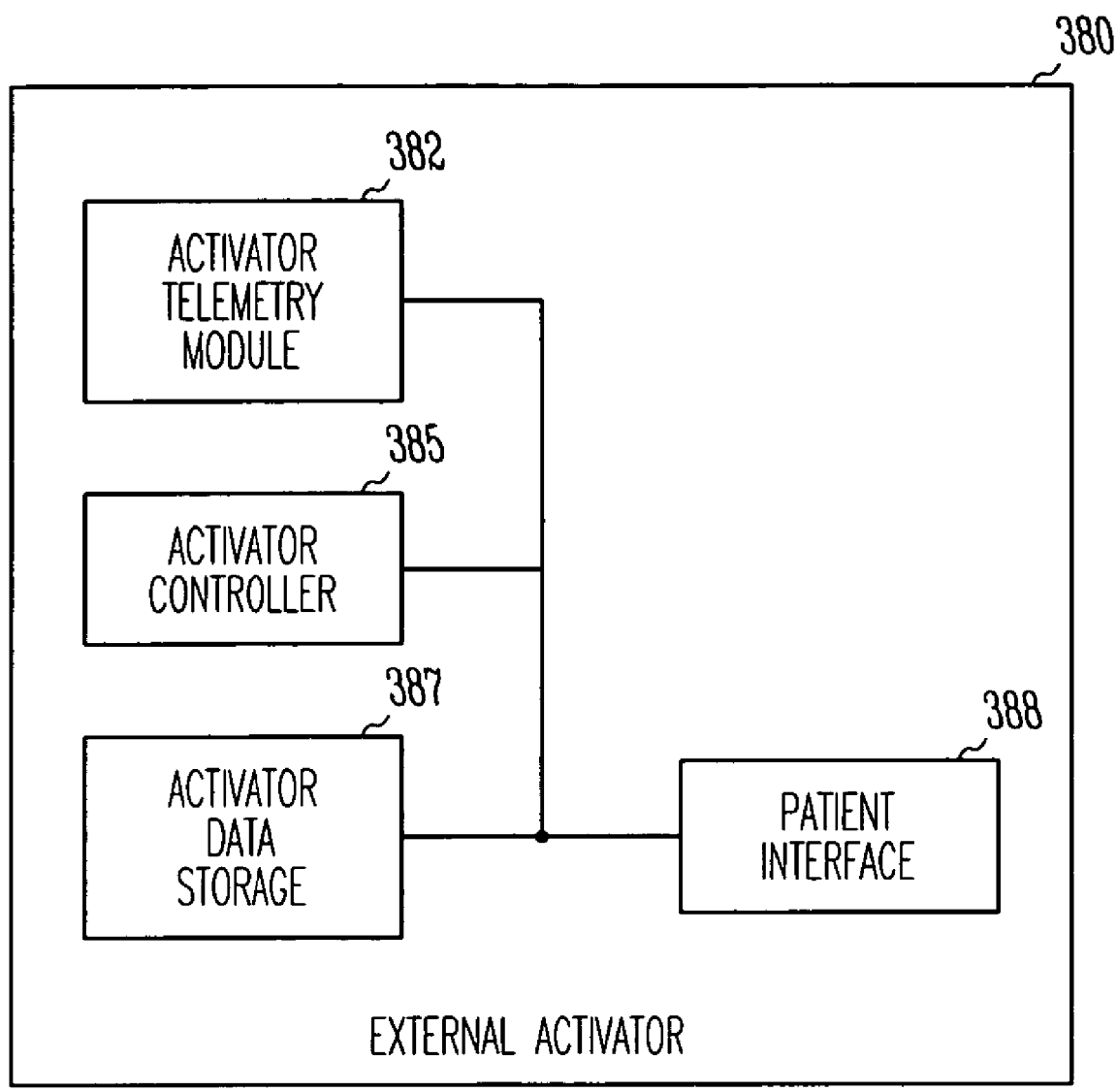
FIG. 3B is a block diagram showing one embodiment of a circuit of an external activator communicating with the implantable medical device.

FIG. 3B is a block diagram showing one embodiment of a circuit of an external activator 380 communicating with implantable medical device 110 via telemetry 160. In one embodiment, activator 380 is an element of external system 170 that directly communicates with implantable medical device 110. In one embodiment, activator 380 is a handheld device provided to the patient for activating a data recording and/or storage process when the patients feels an occurrence of an abnormal condition or symptom. Thus, activator 380 provides an option of a patient-initiated physiological data storage, in place of, or in addition to, a data storage automatically started by when implantable medical device 110 detects an activity of a predetermined type. Activator 380 includes activator telemetry module 382, an activator controller 385, an activator data storage 387, and an patient interface 388.

Activator telemetry module 382 includes an antenna and a transceiver to support two-way communications via telemetry link 160. Activator telemetry module 382 and implant telemetry module 216 form telemetry link 160.

Activator controller 385 controls the overall operation of activator 380. In one embodiment, activator 380 is a computer-based device, such as a personal digital assistant (PDA). Activator controller 385 includes at least portions of the central processing unit and coordinates the activities of all the elements of activator 380.

Activator data storage 387 functions as a buffer or other temporary storage for the physiological signals acquired by implantable medical device 110 and telemetered to activator 380. In one embodiment, activator 380 allows transfer of the acquired physiological signals to a computer or a custom transmitter/modem.

In one embodiment, patient interface 388 includes an input device such as a pushbutton switch used by the patient to enter a command to be sent to implantable medical device 110 to initiate a data storage process. In another embodiment, the patient initiates the recording process by holding activator 380 near implantable medical device 110, such as by holding it against the skin over implantable medical device 110. In this embodiment, activator 380 generates a magnetic field, such as with a magnet, as a command that can be sensed by implantable medical device 110 to initiate the data storage process.

In one embodiment, after the implantation of implantable medical device 110 configured as implantable cardiac monitor 110A, the patient is given activator 380. In one embodiment, the patient decides when implantable cardiac monitor 110A should start and/or stop storing the physiological signals. In another embodiment, implantable cardiac monitor 110A detects predetermined abnormal conditions, such as arrhythmias, and starts/stops storing data automatically. Activator 380, controlled by the patient, provides a back-up to insure the capture of an episode of abnormal conditions when implantable cardiac monitor 110A fails to detect it.

In one embodiment, activator 380 is a device used only when implantable medical device 110 is configured and used as implantable cardiac monitor 110A. In another embodiment, activator 380 is a portable device such as a PDA that is part of external system 170 and is used also when implantable medical device 110 is configured and used as implantable pacemaker 110B, such as in a way discussed in U.S. patent application Ser. No. 10/323,604.

Figure 4A:
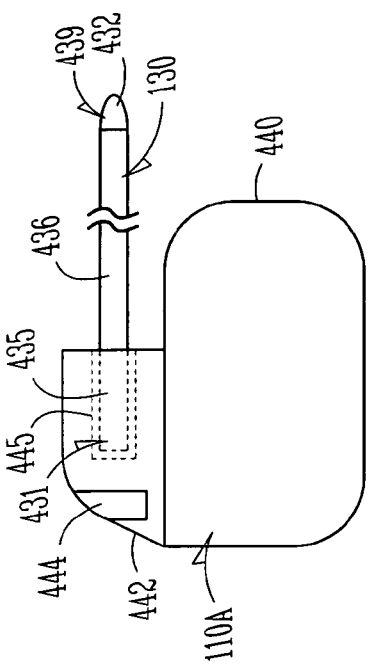
FIG. 4A is an illustration of one embodiment of an apparatus providing the cardiac monitoring system with one sensing electrode.

FIG. 4A is an illustration of one embodiment of adaptor 130 providing cardiac monitoring system 100A with one sensing electrode. Adaptor 130 is connected to implantable medical device 110 configured to and used as implantable cardiac monitor 110A (referenced as 110A in FIGS. 4A-D). Implantable medical device 110/implantable cardiac monitor 110A includes a device body 440 and a header 442 attached to device body 440. Header 442 includes female connector 445 providing for electrical access to the circuit of implantable medical device 110/implantable cardiac monitor 110A encapsulated in device body 440. In one embodiment, as shown in FIG. 4A, a sensing electrode 444 is incorporated into header 442. In one specific example, sensing electrode 444 includes a metal cap or hood that fits over and into header 442. Adaptor 130 includes a proximal end 431, a distal end 439, and an adaptor body 436. Proximal end 431 includes a male connector 435 mating with connector 445. A sensing electrode 432 is incorporated into distal end 439. Connector 435 is electrically connected to sensing electrode 432, and provides for a detachable mechanical and electrical connection between sensing electrode 432 and implantable medical device 110/implantable cardiac monitor 110A. Adaptor body 436 is just long enough for electrode 432 to expose to tissue outside connector 445. In other words, adaptor body 436 has a length that is about the minimum length required for sensing electrode 432 to expose to tissue for proper far-field electrogram sensing. Sensing electrodes 432 and 444 are connected to a pair of differential input of sensing circuit 212 for electrogram sensing.

Figure 4B:
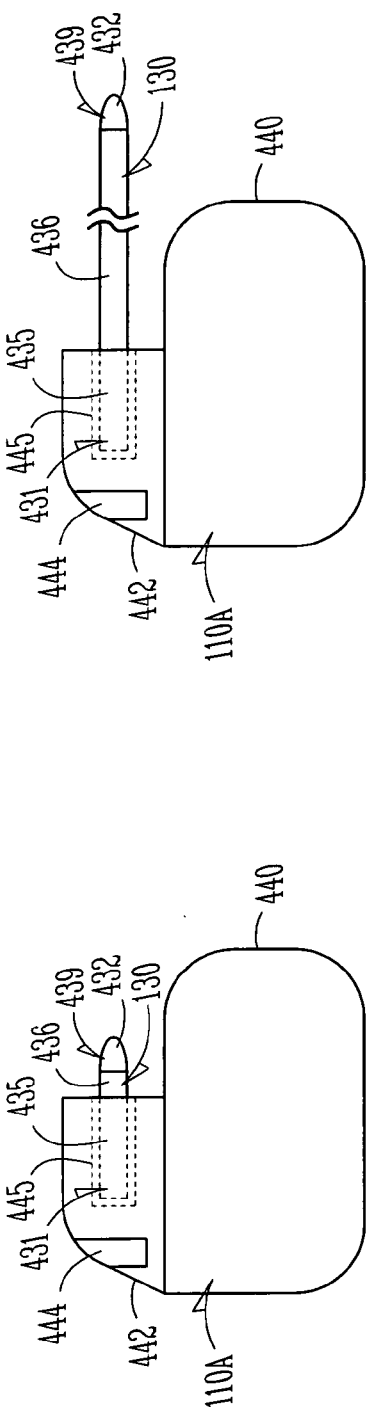
FIG. 4B is an illustration of another embodiment of the apparatus providing the cardiac monitoring system with one sensing electrode.

FIG. 4B is an illustration of another embodiment of adaptor 130 providing cardiac monitoring system 100A with one sensing electrode. Adaptor 130 as shown in FIG. 4B is substantially similar to adaptor 130 as shown in FIG. 4A, except that adaptor body 436 includes a flexible elongate lead. The lead, i.e., a relatively longer adaptor body 436, allows for a longer distance between sensing electrodes 432 and 444 and flexibility for electrode placement.

Figure 4C:
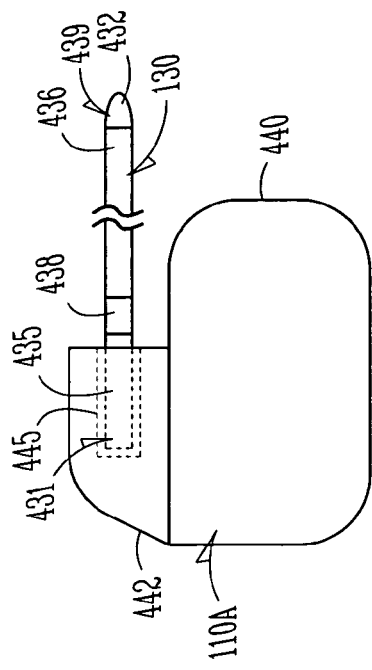
FIG. 4C is an illustration of one embodiment of the apparatus providing the cardiac monitoring system with two sensing electrodes.

FIG. 4C is an illustration of one embodiment of adaptor 130 providing cardiac monitoring system 100A with two sensing electrodes. In this embodiment, header 442 does not include a sensing electrode. Adaptor 130 as shown in FIG. 4C includes a second sensing electrode 438 between proximal end 431 and distal end 439, in additional to electrode 432. Sensing electrodes 432 and 438 are electrically insulated from each other, and electrically connected to connector 435, which provides two separate electrical connections. Thus, sensing electrodes 432 and 438 are separately electrically connected with implantable medical device 110/implantable cardiac monitor 110A through connector 435. Adaptor body 436 includes a lead that has the length and shape that allow electrode 432 to be placed in the location as shown in FIG. 3C (similar to the location of electrode 444 in FIGS. 4A and 4B).

Figure 4D:
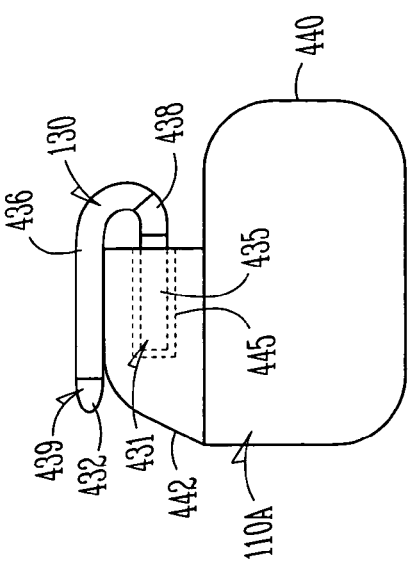
FIG. 4D is an illustration of another embodiment of the apparatus providing the cardiac monitoring system with two sensing electrodes.

FIG. 4D is an illustration of another embodiment of adaptor 130 providing cardiac monitoring system 100A with two more sensing electrodes. Adaptor 130 as shown in FIG. 4D is substantially similar to adaptor 130 as shown in FIG. 4C except that adaptor body 436 includes a more flexible and longer lead.

Adaptors as shown in FIGS. 4A and 4C allow implantable cardiac monitor 110A to be implanted as a "leadless" device, while adaptors as shown in FIGS. 4B and 4D allow more flexibility in electrode placement and in orientation of implantable cardiac monitor 110A within body 102.

Figure 5:
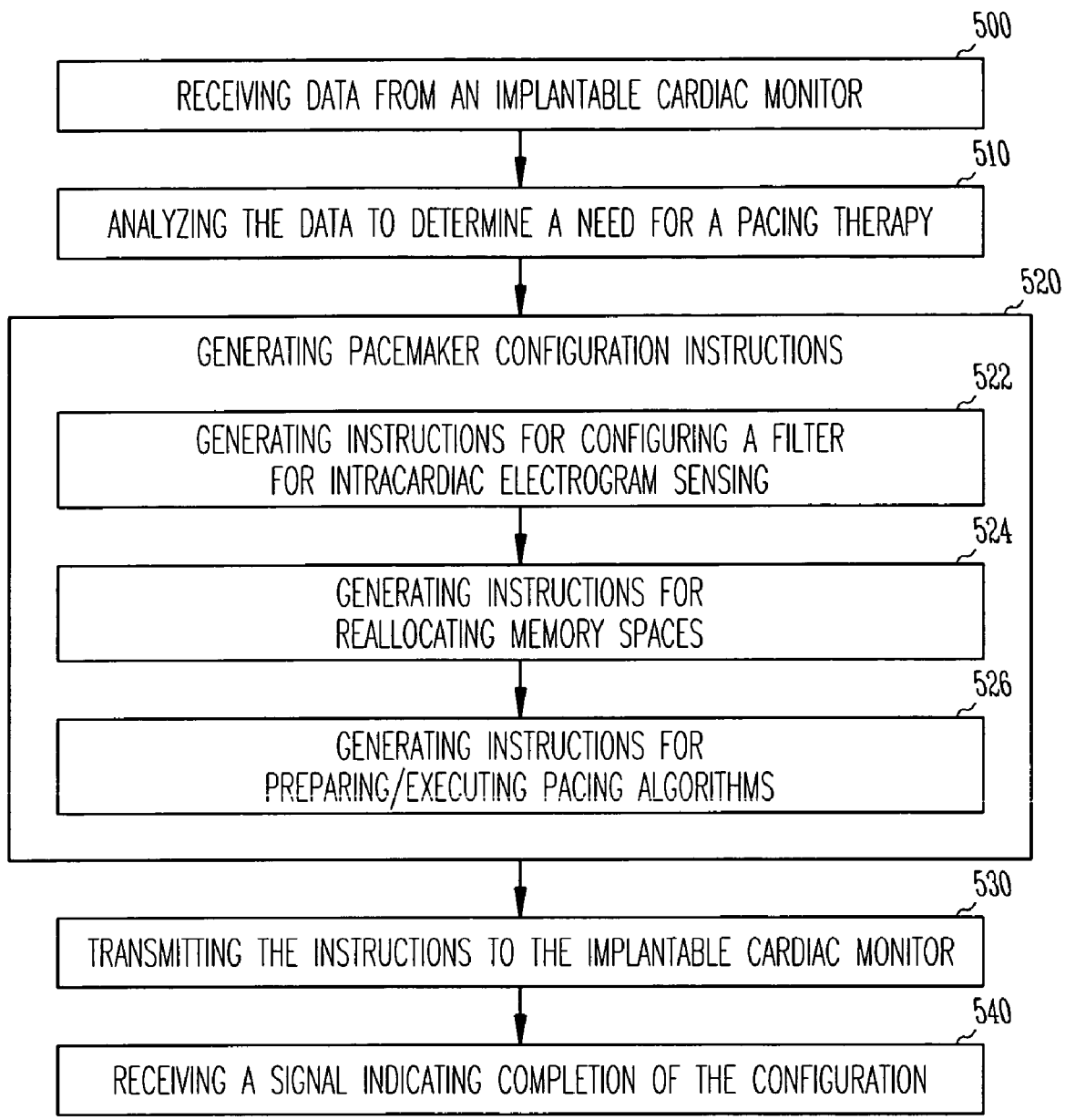
FIG. 5 is a flow chart illustrating an embodiment of a method for upgrading the implantable medical device from the implantable cardiac monitor to the implantable pacemaker.

FIG. 5 is a flow chart illustrating an embodiment of a method for upgrading implantable medical device 110 from implantable cardiac monitor 110A to implantable pacemaker 110B. In one embodiment, the upgrade follows the determination that the patient carrying implantable cardiac monitor 110A will receive a pacing therapy delivered by implantable pacemaker 110B.

External system 170 receives the data acquired by implantable cardiac monitor 110A at 500. In one embodiment, the data includes a far-field electrogram indicative of abnormal cardiac conditions such as cardiac arrhythmia episodes. In another embodiment, the data also includes an acceleration signal indicative of a patient activity level and/or a metabolic level. In another embodiment, the data also includes an activity log reporting predetermined activities detected by implantable cardiac monitor 110A, including time of occurrence and type of each detected activity. External system 170 and/or the user analyze the received data for any indication of a need to provide the patient with a pacing therapy at 510. In one embodiment, the data analysis includes further detection and/or classification of one or more predetermined cardiac arrhythmias. In one embodiment, the user determines a type of pacing therapy, such as a pacing mode and a set of pacing parameters, based on the result of the data analysis.

If it is determined that the patient will receive the pacing therapy, external system 170 generates a set of pacemaker configuration instructions at 520. The instructions are readable by implantable medical device 110, causing a reconfiguration process upgrading implantable cardiac monitor 110A to implantable pacemaker 110B. In one embodiment, external system 170 generates instructions for configuring a filter suitable for intracardiac electrogram sensing at 522. In one specific embodiment, this includes generating instructions for selecting a sensing filter included in implantable medical device 110. In another specific embodiment, this includes generating instructions for configuring a digital filter suitable for sensing an intracardiac electrogram, such as by adjusting filter coefficients defining the frequency response of the digital filter. In one embodiment, external system 170 generates instructions for reallocating memory spaces for storing control code and acquired data at 524, if necessary or desirable. In one embodiment, external system 170 generates instructions for preparing and/or executing at least one pacing algorithm at 526. The pacing algorithm defines how pacing pulses will be delivered according to predetermined logic rules, the patient's intrinsic cardiac depolarization events, and possibly other physiological signals such as the acceleration signal. In one specific embodiment, this includes calling for pacing algorithms stored in external system 170. In another specific embodiment, this includes generating a command to execute one of the pacing algorithms stored in implantable medical device 110.

After generating the set of instructions, external system 170 transmits the instructions to implantable medical device 110 via telemetry at 530, upgrading it from implantable cardiac monitor 110A to implantable pacemaker 110B. In one embodiment, the instructions include authorization information such as a password or a device identification code. The instructions cause the upgrade from implantable cardiac monitor 110A to implantable pacemaker 110B only if and until implantable medical device 110 verifies the authorization information. In another embodiment, external system 170 transmits the authorization information to implantable medical device 110 before transmitting the instructions. Only if and until a permission generated from implantable medical device 110 in response is received, external terminal system 170 transmits the instructions to implantable medical device 110 to cause the upgrade. In one embodiment, the upgrading process completes when external system 170 receives a signal from implantable medical device 110 at 540, indicating that implantable cardiac monitor 110A has been successfully upgraded to implantable pacemaker 110B.

Before a pacing therapy is delivered from implantable pacemaker 110B, adaptor 130 is disconnected from implantable medical device 110 and replaced by lead system 150. In one application, after the determination for upgrading implantable medical device 110 from implantable cardiac monitor 110A to implantable pacemaker 110B, an operation on the patient is performed. The operation includes disconnecting adaptor 130 from implantable medical device 110, implanting the pacing leads of lead system 150, and connecting the pacing leads to implantable medical device 110. Depending on the patient's need and the type of the pacing therapy to be delivered, the pacing lead implantation includes placement of one or more intracardiac leads each having one or more electrodes disposed within the heart, and/or one or more epicardial leads having one or more electrodes disposed on the heart.

Figure 6:
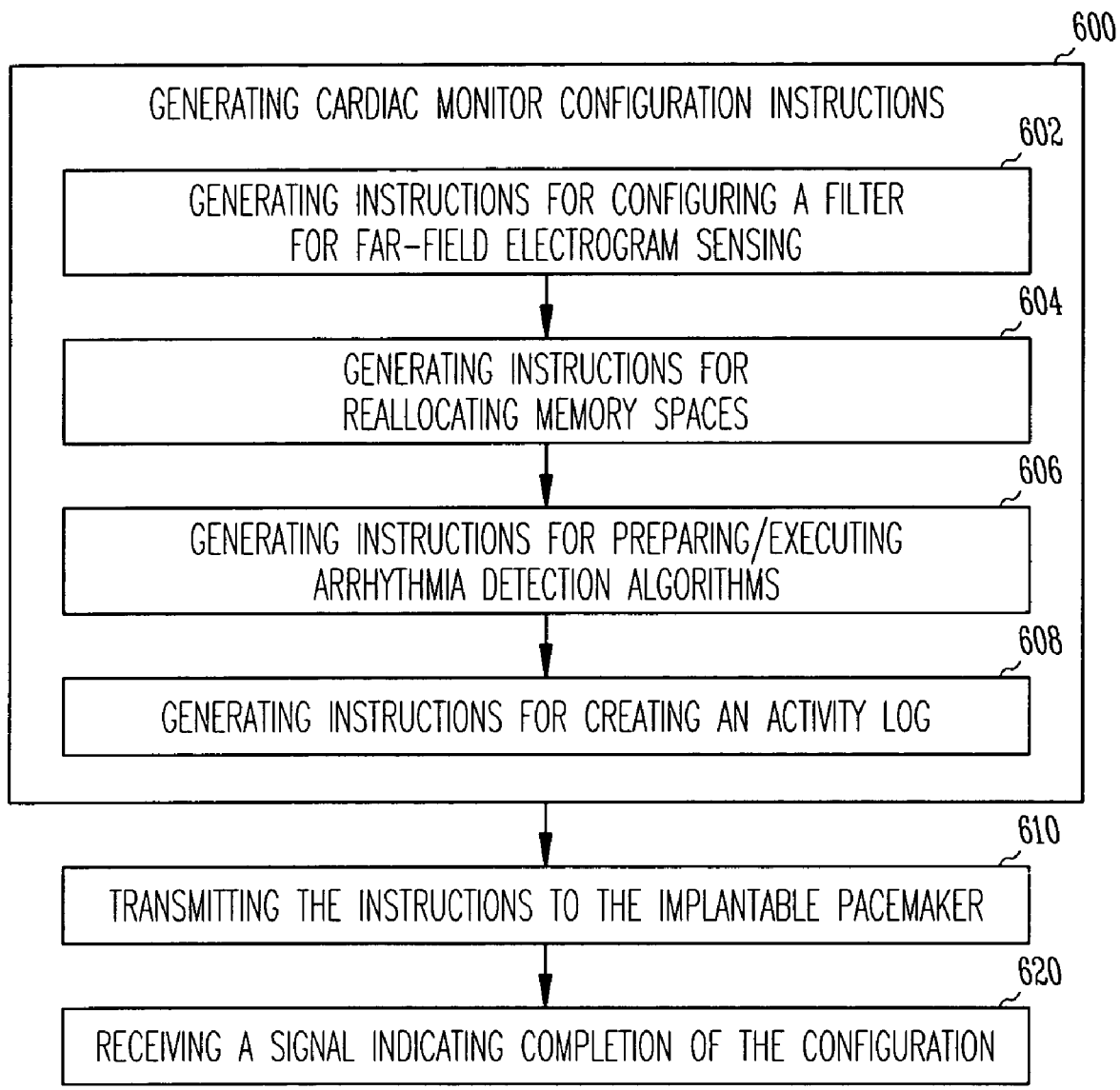
FIG. 6 is a flow chart illustrating an embodiment of a method for converting the implantable medical device from the implantable pacemaker to the implantable cardiac monitor.

FIG. 6 is a flow chart illustrating an embodiment of a method for converting implantable medical device 110 from implantable pacemaker 110B to implantable cardiac monitor 110A. This process is necessary when, for example, implantable medical device 110 is pre-configured as implantable pacemaker 110B by the end of the manufacturing process.

External system 170 generates a set of cardiac monitor configuration instructions at 600. The instructions are readable by implantable medical device 110, causing a reconfiguration process converting implantable pacemaker 110B to implantable cardiac monitor 110A. In one embodiment, external system 170 generates instructions for configuring a filter suitable for far-field electrogram sensing at 602. In one specific embodiment, this includes generating instructions for selecting a sensing filter included in implantable medical device 110. In another specific embodiment, this includes generating instructions for configuring a digital filter suitable for sensing a far-field electrogram, such as by adjusting filter coefficients defining the frequency response of the digital filter. In one embodiment, external system 170 generates instructions for reallocating memory spaces for storing control code and acquired data at 604, if necessary or desirable. In one embodiment external system 170 generates instructions for preparing and/or executing at least one activity detection algorithm at 606. In one embodiment, the activity detection algorithms includes an arrhythmia detection algorithm defining how the far-field electrogram is analyzed by implantable cardiac monitor 110A to detect one or more predetermined arrhythmia types. In one specific embodiment, this includes calling for arrhythmia detection algorithms stored in external system 170. In another specific embodiment, this includes generating a command to execute an arrhythmia detection algorithm stored in implantable medical device 110. In one further embodiment, only electrogram recorded during detected arrhythmic episodes will be stored. In one embodiment, external system 170 generates instructions for creating an activity log at 608. The activity log includes detections of episodes of the predetermined activities, such as the detected arrhythmic episodes, each with indications of the time of the occurrence and the type of the activity.

After generating the set of instructions, external system 170 transmits the instructions to implantable medical device 110 via telemetry at 610, converting it from implantable pacemaker 110B to implantable cardiac monitor 110A. In one embodiment, the instructions include authorization information such as a password or a device identification code. The instructions cause the conversion from implantable pacemaker 110B to implantable cardiac monitor 110A only if and until implantable medical device 110 verifies the authorization information. In another embodiment, external system 170 transmits the authorization information to implantable medical device 110 before transmitting the instructions. Only if and until a permission generated from implantable medical device 110 in response is received, external system 170 transmits the instructions to implantable medical device 110 to cause the conversion. In one embodiment, the conversion process completes when external system 170 receives a signal from implantable medical device 110 at 620, indicating that implantable pacemaker 110B has been successfully converted to implantable cardiac monitor 10A.

Before recording the far-field electrogram, adaptor 130 is connected to implantable medical device 110. In one embodiment, adaptor 130 is connected to implantable medical device 110 during the implantation of implantable medical device 110 (configured as implantable cardiac monitor 110A).

In one embodiment, either or both of methods illustrated in FIGS. 5 and 6 are implemented as software installed in external system 170. In one embodiment, external system 170 includes a computer or a computer-based system. Computer-executable instructions causing the computer or the computer-based system to perform either or both of methods illustrated in FIGS. 5 and 6 are stored in a computer readable medium. In one specific embodiment, external system 170 includes programmer 370, a computer-based device. The computer-executable instructions are installed in programmer 370 before the user uses programmer 370 to configure implantable medical device 110, such as upgrading implantable cardiac monitor 110A to implantable pacemaker 110B, or converting implantable pacemaker 110B to implantable cardiac monitor 110A.

It is to be understood that the above detailed description is intended to be illustrative, and not restrictive. For example, implantable medical device 110 may be configured to another type of medical device in addition to implantable cardiac monitor 110A and implantable pacemaker 110B. Other embodiments, including any possible combinations of the elements of the apparatus and methods discussed in this document, will be apparent to those of skill in the art upon reading and understanding the above description. The scope of the invention should, therefore, be determined with reference to the appended claims, along with the full scope of equivalents to which such claims are entitled.

What is claimed is:

1. An implantable medical device, comprising:
a sensing circuit adapted to sense an electrogram, the sensing circuit having a set of cutoff frequencies for filtering the sensed electrogram, the set of cutoff frequencies programmed to be a first set of values and a second set of values at different times, the first set of values suitable for far-field electrogram sensing, the second set of values suitable for intracardiac electrogram sensing and different from the first set of values;
a pacing circuit; and
a processor coupled to the sensing circuit and the pacing circuit, the processor including a cardiac monitor controller that is upgradeable to a pacemaker controller by programming the implantable medical device to configure the implantable medical device from an implantable cardiac monitor to an implantable pacemaker,
wherein the implantable medical device is configured to operate as the implantable cardiac monitor and the implantable pacemaker at said different times, the pacing circuit is adapted to be inactive when the implantable medical device is configured to be the implantable cardiac monitor and capable of producing pacing pulses when the implantable medical device is configured to be the implantable pacemaker, and the set of cutoff frequencies of the sensing circuit is programmed to the first set of values while the pacing circuit is inactive and programmed to the second set of values while the pacing circuit is capable of producing pacing pulses.

2. The implantable medical device of claim 1, wherein the sensing circuit comprises a band-pass digital filter having programmable filter coefficients.

3. The implantable medical device of claim 1, wherein the set of cutoff frequencies comprises a low cutoff frequency and a high cutoff frequency, the low cutoff frequency programmed to a first low cutoff frequency value while the pacing circuit is inactive and programmed to a second low cutoff frequency value while the pacing circuit is capable of producing pacing pulses, the high cutoff frequency programmed to a first high cutoff frequency value while the pacing circuit is inactive and programmed to a second high cutoff frequency value while the pacing circuit is capable of producing pacing pulses.

4. The implantable medical device of claim 3, wherein the first low cutoff frequency value is in a range of 0.5 Hz to 10 Hz and the first high cutoff frequency value is in a range of 30 Hz to 100 Hz.

5. The implantable medical device of claim 3, wherein the second low cutoff frequency value is in a range of 10 Hz to 30Hz and the second high cutoff frequency value is in a range of 60 Hz to 150 Hz.

6. The implantable medical device of claim 1, wherein the processor comprises:
  a microprocessor; and
  a memory circuit coupled to the microprocessor, the memory circuit includes a random access memory containing at least a portion of a control code, including one of a cardiac monitor control code and a pacemaker control code.

7. The implantable medical device of claim 6, wherein the sensing circuit further comprises an activity sensor circuit to sense at least one physical activity level.

8. The implantable medical device of claim 7, wherein the memory circuit comprises a data storage space allowing storage of one or more of an electrogram, the at least one physical activity level, and an activity log reporting detections of predetermined activities.

9. The implantable medical device of claim 8, wherein the processor further comprises an activity detector to detect the predetermined activities from one or more of the electrogram and the at least one physical activity signal.

10. The implantable medical device of claim 9, wherein the activity detector comprises an arrhythmia detector to detect at least one predetermined type of arrhythmia from the electrogram.

11. The implantable medical device of claim 1, wherein the processor comprises:
  a microprocessor; and
  a memory circuit including a read-only memory configured to store firmware and a random-access memory configured to store upgradeable software, wherein at least a portion of the upgradeable software is updated when the cardiac monitor controller is upgraded to the pacemaker controller.

12. The implantable medical device of claim 11, wherein the memory circuit includes a control code providing for a safety operation mode when the cardiac monitor controller is being upgraded to the pacemaker controller.

13. The implantable medical device of claim 12, wherein the pacemaker controller is further convertible to the cardiac monitor controller by programming the implantable medical device.

14. The implantable medical device of claim 13, wherein the random-access memory comprises data storage space reallocated when the cardiac monitor controller is upgraded to the pacemaker controller and when the pacemaker controller is converted to the cardiac monitor controller.

15. The implantable medical device of claim 1, comprising an implant telemetry module adapted to receive device configuration instructions via telemetry, the device configuration instructions causing the cardiac monitor controller to be upgraded to the pacemaker controller.

16. The implantable medical device of claim 15, wherein the device configuration instructions comprise authorization information, and the processor comprises a configuration authorization module adapted to permit the cardiac monitor controller to be upgraded to the pacemaker controller upon verification of the authorization information.

17. The implantable medical device of claim 16, wherein the configuration authorization module is adapted to permit the cardiac monitor controller to be upgraded to the pacemaker controller upon receiving a device identification code uniquely identifying a device intended to be configured.

18. The implantable medical device of claim 15, wherein the processor comprises a configuration authorization module adapted to generate a permission signal upon verifying authorization information in an authorization signal received by the implantable medical device.

19. The implantable medical device of claim 1, wherein the sensing circuit is adapted to sense one or more signals indicative of one or more of a physical activity level and a metabolic level.

20. The implantable medical device of claim 1, comprising an implantable cardiac resynchronization device converted from an implantable cardiac monitor after the cardiac monitor controller is upgraded to the pacemaker controller.

* * * * *